United States Patent
Shearer et al.

(10) Patent No.: US 6,569,807 B1
(45) Date of Patent: May 27, 2003

(54) MYCOHERBICIDAL COMPOSITIONS AND METHODS OF PREPARING AND USING THE SAME

(75) Inventors: Judy F. Shearer, Vicksburg, MS (US); Mark A. Jackson, Peoria, IL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/138,579

(22) Filed: May 6, 2002

(51) Int. Cl.[7] .............................................. A01N 63/04
(52) U.S. Cl. ....................................... 504/117; 504/150
(58) Field of Search ................................ 504/117, 150

(56) References Cited

U.S. PATENT DOCUMENTS

| | | |
|---|---|---|
| 4,594,809 A | 6/1986 | Ower et al. |
| 5,068,105 A | 11/1991 | Lewis et al. |
| 5,178,642 A | 1/1993 | Janerette |
| 5,538,890 A | 7/1996 | Sands et al. |
| 5,945,099 A | 8/1999 | Marshall ..................... 504/117 |

OTHER PUBLICATIONS

Greaves, M. P. "Microbial Herbicides" Pesticide Outlook. 4(4):20–22. Nov. 1993.*
Sutton, B.C., Pucciniopsis, Mycoleptodiscus and Amerodiscosiella, Trans. Br. Mycol. Soc. 60(3), 525–526 1973.
Shearer, J. F., Effect of a New Growth Medium on Mycoleptodiscus Terrestris (Gerd.) Ostazeski, ERDC-TN-APCRP-BC-04, Jun. 2002, 7 pp.

* cited by examiner

Primary Examiner—S. Mark Clardy
(74) Attorney, Agent, or Firm—Earl H. Baugher, Jr.; Allen Kipnes

(57) ABSTRACT

A mycoherbicidal composition prepared from a microsclerotium of a fungal pathogen in an aquatic weed population control effective amount to achieve aquatic weed population and growth control in combination with a suitable carrier. The present invention is further directed to a method of using the composition to control aquatic weed populations and a method of preparing the fungal microsclerotium.

28 Claims, No Drawings

MYCOHERBICIDAL COMPOSITIONS AND METHODS OF PREPARING AND USING THE SAME

STATEMENT OF GOVERNMENT INTEREST

The invention described herein may be manufactured and used by or for the Government of the United States of America for governmental purposes without the payment of any royalties thereon or therefor.

FIELD OF THE INVENTION

The present invention relates generally to bioherbicides suitable for controlling a population of target aquatic weeds, and more particularly to mycoherbicidal compositions, methods of preparing the same, and methods for controlling the population of target aquatic weeds.

BACKGROUND

Many of the world's waterways and water systems have become infested with aquatic weeds to the detriment of local wildlife and water traffic. Typically, the aquatic weeds are of non-indigenous origin unintentionally introduced into an area with little or no natural enemies. In other instances, excess nitrates from runoffs have enabled the aquatic weeds to thrive and spread. These infestations can effectively choke local ecosystems comprising native fauna and flora, and disrupt water traffic and drainage. Their ability to survive under less than desirable conditions and their high growth rate has enabled aquatic weeds to circumvent many of the currently available population control measures.

The more common population control measures are chemical herbicides and mechanical harvesters. Chemical herbicides pose health hazards to both humans and other non-targeted plants and animals. In many places, aquatic weeds have developed resistance to certain chemical herbicides further complicating the control of their population. Mechanical harvesters have also been used with limited success, and provide marginal population control. Most mechanical harvesters are expensive, and require frequent usage to achieve even modest population control.

A more environmentally safe population control measure that is also cost-efficient, relies on biological agents in the form of mycoherbicides. Mycoherbicides are typically formulated with one or more fungal pathogens or metabolites, or both thereof with herbicidal activity. The fungal pathogens are typically specific to infecting a certain spectrum of plant types, thus providing useful targeted delivery. One fungal pathogen, *Mycoleptodiscus terrestris* (Gerd.) Ostazeski, has been studied for its potential in controlling populations of target aquatic weeds. *M. terrestris* is a fungus classified in the family Dematiaceae of the Hyphomycetes class within the subdivision Deuteromycotina. There are about ten known species of Mycoleptodiscus and each are classified according to the presence of appendages on the spores, orientation of the appendages (e.g., polar, polar and lateral) on the spores, location of the appendages (e.g., apex or apex and base) on the spores, and spore septation and size.

Current processes and compositions for the preparation of a mycoherbicide have been limited to the preparation and use of *M terrestris* mycelium. However, the mycelium of *M. terrestris* exhibits limited viability, poor stability, and a short shelf life. The ability of *M. terrestris* mycelium to control weed populations can diminish rapidly under certain conditions typically associated with normal storage and handling. These shortcomings have required high application rates and immediate use to obtain adequate population control efficacy against aquatic weeds.

It would be an advance in the art of bioherbicides to develop a mycoherbicidal composition, which can be applied either in wet or dry form, comprising an effective population control agent efficacious against a broad range of aquatic weeds including hydrilla. It would be a further advance in the art to develop a mycoherbicidal composition with enhanced biological viability and stability, specifically comprising a fungal pathogen as the population control agent that is extremely desiccant-tolerant, is capable of germinating both sporogenically and vegetatively, and is highly efficacious against hydrilla and other aquatic weeds, while being easy and relatively inexpensive to prepare and to use. It would also be desirable to provide a method of preparing such fungal pathogens in the form of a microsclerotium that can efficiently and effectively maximize the biomass production thereof.

SUMMARY

The present invention is directed generally to mycoherbicidal compositions, and methods of preparing and using the same for aquatic weed population and growth control. The mycoherbicidal composition is comprised of a fungal pathogen in the form of a stable melanized hyphal aggregate or microsclerotium, that is extremely desiccant-tolerant and highly viable, is capable of germinating both sporogenically and vegetatively, and is efficacious against hydrilla and other aquatic weeds. The fungal microsclerotium avoids many of the problems typically associated with mycelium-based pathogens including poor stability, limited viability, and short shelf life. The desiccant-tolerant microsclerotium maintains enhanced viability for providing improved germination rate, ease of storage and handling and better shelf life.

The present composition may be applied in wet or dry form suitable for effective dissemination over an area infested by target aquatic weeds including, but not limited to, those selected from *Hydrilla verticillata* (L.f.) Royle ("hydrilla"), *Myriophyllum spicatum* L. ("Eurasian watermilfoil"), *Egeria densa* L. ("Brazilian Elodea"), and combinations thereof.

In one particular aspect of the present invention, there is provided a mycoherbicidal composition suitable for controlling the growth and population of target aquatic weeds, which comprises an aquatic weed population control effective amount of a microsclerotium of a fungal pathogen. Optionally, the composition may further include a suitable carrier. The present invention may include fungal pathogens selected from strains of the genera Fusarium, Cercospora, Alternaria, Mycoleptodiscus, and the like. In a preferred form of the present invention, the fungal pathogen is *Mycoleptodiscus terrestris* (*M. terrestris*).

In another particular aspect of the present invention, there is provided a method for controlling the growth and population of target aquatic weeds, where the method comprises applying an aquatic weed population control effective amount of the mycoherbicidal composition of the present invention to a treatment site in which the fungal pathogen can contact and infect the target aquatic weeds.

In a further aspect of the present invention, there is provided a method for preparing a microsclerotium of a fungal pathogen having aquatic weed population control activity, where the method comprises growing the fungal pathogen under suitable growth conditions sufficient to compel the fungal pathogen to form a microsclerotium.

DETAILED DESCRIPTION

In accordance with the present invention, a mycoherbicidal composition is provided for controlling the growth and population of aquatic weeds. The mycoherbicidal composition generally comprises a target aquatic weed population control effective amount of a microsclerotium or melanized hyphal aggregate of a fungal pathogen having aquatic weed population control activity and, optionally, may further include a suitable carrier. The microsclerotium of the fungal pathogen present in the mycoherbicidal composition of the present invention is capable of tolerating conditions associated with low moisture and exhibits improved viability even after drying and storage.

In addition, the microsclerotium of the fungal pathogen is capable of germinating both vegetatively to yield mycelium as a primary inoculum for attacking the target aquatic weed, and sporogenically to yield spores for employment as a secondary inoculum. The ability of the microsclerotium to germinate sporogenically advantageously extends the efficacy and duration of the present compositions containing the same against the aquatic weed. The ability to sporulate enables the fungal microsclerotium to be used as a preventative against impending re-infestations of the aquatic weed.

As used herein the term "microsclerotium" refers to the resting state or body of certain fungi, which is capable of resisting environmentally harsh conditions including extreme heat or cold, unfavorable soil, severe weather, ultraviolet light, damaging chemicals, low-moisture conditions, and the like. The microsclerotium may come in different forms such as a sclerotium (i.e., a medulla surrounded by a cortex) or as an agglomerated group of cells.

The present invention encompasses microsclerotia of a fungal pathogen selected from those including, but not limited to, *Mycoleptodiscus terrestris* (*M. terrestris*), *Fusarium roseum* (Culmorum), *Cercospora rodmanii*, *Cercospora piaropi*, and *Alternaria alternantherae*, that are shown to be efficacious against a range of aquatic weeds. Preferred target weeds include *Hydrilla verticillata* (L.f.) Royle ("hydrilla"), *Myriophyllum spicatum* L. ("Eurasian watermilfoil"), *Egeria densa* L. (")Brazilian Elodea"), *Eichhornia crassipes* ("water hyacinth"), and *Alternanthera philoxeroides* ("alligator weed").

In a preferred embodiment of the present invention, the fungal pathogen is a *Mycoleptodiscus terrestris* (*M. terrestris*). *M terrestris* is known to be especially efficacious against aquatic weeds including, but not limited to, *Hydrilla verticillata* (L.f.) Royle ("hydrilla"), *Myriophyllum spicatum* L. ("Eurasian watermilfoil"), *Egeria densa* L. ("Brazilian Elodea"), and the like. In particular, the *M. terrestris* fungal pathogen exhibits rapid onset of disease in hydrilla, and is a safe and effective bioherbicide against a range of aquatic weeds Upon infection, the foliage tissue of the infected plant undergoes the process of chlorosis. The infected plant first begins to lose color in about four to seven days after onset of disease, and then begins to disintegrate in about seven to ten days after onset. The *M. terrestris* fungal pathogen effectively destroys the cellular integrity of plant tissues, leading to the eventual collapse of the entire plant.

The present invention is further directed to a method of making the microsclerotium form of the fungal pathogen for incorporation into the present mycoherbicidal compositions. The fungal pathogen can be isolated or obtained by using inoculum extracted from deposited culture specimens or extracted from infected plants through culturing techniques as known in the art. The microsclerotium of the fungal pathogen can be easily and abundantly prepared in culture using conventional techniques in fermentation technology. Such fermentation technology includes solid and liquid methods.

In the present invention, the fungal pathogen such as *M. terrestris* may be grown for a sufficient time at a suitable temperature to scale up production and generate a desired fungal biomass. Thereafter, the fungal pathogen can then be induced through exposure to suitable growth conditions and environments that cause the fungal pathogen to form microsclerotia.

In one form of the present invention, the fungal pathogen is exposed to a nutrient-rich growth media preferably in the form of a aqueous media, having a microsclerotium forming effective concentration or amount of nutritive substances, including nitrogen sources and carbon sources, that are sufficient to simultaneously support the growth of the fungal pathogen and stimulate the differentiation or aggregation of the fungal biomass into microsclerotia. In the present invention, the term "a microsclerotium forming effective concentration or amount" is defined as any such quantity of nutritive substances, including nitrogen sources and carbon sources, sufficient to induce the mycelia of the fungal pathogen to form into the desired microsclerotia such as by aggregation or differentiation.

Examples of nitrogen sources include corn steep liquor, cottonseed meal, wheat flour, soy flour, yeast extract, hydrolysates of animal or plant proteins, corn flour, digestible proteins, amino acids and the like, and examples of carbon sources include monosaccharides (e.g., glucose), disaccharides, polysaccharides, vegetable oils, animal fats, complex carbohydrates, and the like. It will be understood that the growth medium of the present invention may further include other active ingredients that can effectively facilitate the growth and formation of the desired microsclerotium of the fungal pathogen.

It will be understood that prior to the formation of the microsclerotia, the fungal pathogen may be grown to generate a sufficient fungal biomass in a suitable conventional culture media under suitable temperature and growth conditions. Any growth media in which the desired fungal pathogen will effectively grow may be used. Agents to suppress sporulation and antibiotic compounds to ensure biological purity may be added to the culture media during the production process.

To scale up the production of the fungal biomass, the culture media may be inoculated with an inoculum extracted from pure stock cultures. The pure stock cultures may be produced through plating the fungal pathogen on a suitable nutritive substrate such as potato dextrose agar (PDA). The fungal pathogen is allowed to grow for a sufficient time under controlled conditions to produce the inoculum comprised primarily of mycelia.

Thereafter, fungal biomass is inoculated into the corresponding culture media preferably comprising a basal medium and suitable nutrients, utilizing conventional shake flask culture techniques and suitable fermentation conditions to produce the fungal biomass. Preferably, the culture media is inoculated with the inoculum in an amount of about 1–10% of the total culture media. The fungal biomass is preferably grown at a temperature of from about 20°–35° C., more preferably at a temperature of about 28° C., in a rotary shaker incubator at an agitation rate of about 300 rpm for a sufficient time to yield an ample biomass comprising mycelia. The incubation period for completing the fermentation ranges from about one to six days, depending on the volume of the mycelial biomass desired. If more fungal biomass is desired, the cultures may be serially transferred to one or more larger shake flasks or fermenters containing fresh culture media. This biomass production process may be repeated until the desired biomass size is achieved.

Once the desired fungal biomass is achieved, the resulting fungal pathogen mycelial biomass is then harvested and inoculated into a larger culture vessel containing a nutrient-rich growth media comprising a basal medium and a microsclerotium forming effective concentration of nitrogen and carbon sources. The exposure of the fungal biomass to the nutrient-rich growth media induces the hyphae or mycelia to aggregate and differentiate into the microsclerotia. The fungal biomass is preferably incubated under suitable fermentation conditions for temperature, pH, aeration, agitation, back pressure, and dissolved oxygen in order to optimize the production of the microsclerotia.

For cultures of *M. terrestris* fungal pathogen, the fungal biomass is grown in the growth media comprising a basal medium and a microsclerotium forming effective concentration of a nitrogen source such as proteins and amino acids, and a carbon source such as glucose, as described in Example 1. The fungal biomass is preferably grown at room temperature, more preferably at a temperature of from about 25°–30° C., and most preferably at about 28° C., in a rotary shaker incubator for a sufficient time to yield the microsclerotia of *M. terrestris*. The incubation period for completing the fermentation can range from about two to nine days, depending on the volume of the microsclerotia desired.

Upon producing the sufficient microsclerotial biomass, the resulting fungal slurry containing the microsclerotia may be incorporated into the present mycoherbicidal compositions in accordance with the present invention.

In another form of the present invention, the microsclerotia may also be harvested through suitable means including, but not limited to, filtration and centrifugation. Thereafter, the harvested microsclerotia may be used for formulation into the present compositions. The resulting fungal slurry containing the microsclerotia may be admixed with filter media such as HYFLO diatomaceous earth available from Lompoc, Calif., and dried through vacuum filtration. The dried microsclerotial biomass (i.e., filter cakes or pellets) may be optionally admixed with a suitable carrier (wet or dry) for formulating into the present mycoherbicidal compositions as will be described hereinafter.

In another embodiment of the present invention, the fungal slurry containing the microsclerotia may be dried onto a primary agronomically acceptable carrier, e.g., vermiculite, whereby the fungal microsclerotium is absorbed onto the carrier. If desired, the fungal slurry may be used as the concentrate for the mycoherbicidal composition for application in the form of a wet preparation. The actual concentration of the microsclerotium in the composition is not particularly critical, and is a function of practical considerations such as the properties of the vehicle or carrier, and the method of application. For purposes of formulation and application, a "population control effective amount" is defined to mean any such quantity of microsclerotia sufficient to infect the target aquatic weeds and achieve the desired level of weed population control.

In one example, the microsclerotium of the present invention may be formulated with biocarriers as disclosed in U.S. Pat. No. 5,945,099, Mycoherbicidal Delivery Compositions, Preparation and Methods for Controlling Aquatic Weeds, to Marshall, Aug. 31, 1999, the entire content of which is incorporated herein by reference. The biocarriers provide the matrix structure for the composition of the present invention, and may also serve as a nutrient source that may be beneficial to the fungal pathogen carried therein. During application, the present compositions formed by the biocarriers slowly dissolve, the fungal pathogen is suspended in the water near the weed in such a form that it adheres to the plant, thereby allowing sufficient contact time for inducing infection.

The microsclerotium of the present invention is preferably formulated to yield mycoherbicidal compositions suitable for large area applications. The mycoherbicidal compositions may be utilized effectively in a range of formulations, including agronomically acceptable adjuvants and carriers normally employed for facilitating dispersion of active agents for weed population control. It will be understood that the dosage, formulations, mode of application of a chemical agent, and other variables may affect activity of the mycoherbicidal compositions of the present invention in any given application. Thus, the described mycoherbicidal composition may be formulated as a suspension or dispersion, in aqueous or non-aqueous media, as a dust, as a wettable powder, as an emulsifiable concentrate, as a granule, or as any of several other known types of formulations, depending on the desired mode of application as known by those skilled in the art. The compositions may be applied as sprays, dust, or granules directly to the plant or at sites where herbicidal or weed population control activity is desired.

The addition of materials to the compositions to alter the density of the final products is also contemplated, such as high-density materials that cause the products to sink, and low-density materials that cause the products to float. A combination of two or more compatible weed pathogenic fungi, or a fungal pathogen combined with other compatible biological control agents, may be included, where feasible, to broaden the weed population control properties of the products of this invention. Adjuvants or other additives such as agrochemicals, biopesticides or mixtures thereof, may also be included.

The microsclerotium may be added to the carrier as described above, with or without wetting agents or humectants or additional absorptive agents such as silica or clay. Other possible carriers include dispersants, surfactants, emulsifiers, gas-producing disintegrants, glidants, and slip agents. Suitable gas producing disintegrants include effervescing agents such as sodium or potassium bicarbonate with a food grade acid such as citric acid, for example.

The microsclerotia of the present composition may be formulated as dry flowables, water dispersible granules, broadcast granules, suspensions, emulsions, tablets, briquettes, and the like. When the composition is formulated as a granule, tablet or briquette, it has a good hardness and does not tend to crumble or dust, thereby reducing user exposure to the microsclerotium. The composition may be readily dispersed in water for spray application or the like.

The mycoherbicidal composition in the form including, but not limited to, granules, tablets and the like, may be applied to an area, locale or treatment site by applying directly to the environment (e.g., bodies of water) where the aquatic weeds are present or on the aquatic weed itself. Preferably, the compositions are applied at specific sites (e.g., boat ramps and docks, swimming areas, water intake areas, navigation channels, and the like) for controlling the population of the aquatic weeds using conventional herbicide application equipment. When an effective amount of the composition is applied to the aquatic weeds, the fungal pathogen will infect the target weed, thereby controlling its growth or killing it. An effective amount is that quantity of the composition, which will result in a significant level of damage as compared to an untreated group. The actual amount may vary with the particular weed pathogen, the maturity and susceptibility of the target weed, the degree of population control activity sought, and other conditions. The selection of the proper effective amount of the composition to be applied, however, is within the expertise of one skilled in the art.

In one mode of treatment, the mycoherbicidal composition may be applied after emergence of the foliage of the aquatic weed. In another mode of treatment, the mycoherbicidal composition may be applied during the active growth cycle of the aquatic weed. For example, the application dosages may be applied to the water or the weed foliage in amounts of from about 10 g–100 Kg per acre of the target area to be treated, depending on the severity of the infestation, the condition of the target area, water conditions, and the like.

When the target weed is hydrilla, and the fungal pathogen is *M. terrestris*, it is preferable to apply the composition of the present invention early in the growing season, perhaps because the young plants are more susceptible to ingress of *M. terrestris*. Temperature may also be a factor in disease development as the optimum temperature for fungal growth is from 22–28° C. Cooler temperatures earlier in the growing season may be more favorable to fungal growth than are elevated temperatures later in the season. The application rate may be in the range of at least ten microsclerotia/cm$^2$ of target area. Preferably, the application rate may be in the range of from about 10–10,000 microsclerotia/cm$^2$, and more preferably from about 100–2,000 microsclerotia/cm$^2$. Application rates less than 100 microsclerotia/cm$^2$ are primarily useful in a formulation including a second herbicide.

EXAMPLE 1

Preparation of *M. terrestris* Microsclerotia

A fungal strain of *M. terrestris* was isolated from hydrilla growing in Texas. Spores produced by this strain each include a single appendage at both the apex and the base thereof. The spores are septate with each including one median septa. Each spore measures from about 20×5 $\mu$m to 35×7 $\mu$m. The appendages are each often observed to be bifurcated at the tips, which is atypical in this species. The fungal strain was observed to be particularly virulent against hydrilla. The fungal strain was deposited on Feb. 22, 2002 in the Agricultural Research Service Patent Culture Collection (NRRL), Peoria, Ill., under the provisions of the Budapest Treaty, and assigned the number NRRL 30559. Samples of the fungal strain may also be obtained from ERDC Waterways Experiment Station in Vicksburg, Miss., under culture number WES030801.

Stock cultures were prepared by plating *M. terrestris* onto potato dextrose agar plates (PDA), and incubated at room temperature for about one to two weeks. Plugs 1 mm in diameter were cut from the cultivated fungal colony. Excess plugs may be cryogenically stored in vials containing 10% glycerol at −80° C. and may be retrieved as needed for additional plating. The plugs were plated onto the PDA and grown at room temperature for about fourteen days to produce inoculum for subsequent fermentation in a liquid culture media. After fourteen days, the resulting PDA cultures comprised generally of mycelia, were chopped into 1-mm pieces and placed into sterile de-ionized water.

A culture media was prepared by adding to a first vessel or a shake flask, a microbial nutrient or nitrogen source selected from SOLULYS AST, a corn steep powder product produced by Roquette of Lestrum, France, in an amount of 1.5% w/v of the total culture media; PHARMAMEDIA, in an amount of from about 3–6% w/v of the total culture media; or PROFLO in an amount of from about 3–6% w/v of the total culture media, the latter two are each a cottonseed meal product produced by Traders Protein of Memphis, Tenn.

A basal medium was prepared with the following components: $KH_2PO_4$ (4 g/L), $MgSO_4.7H_2O$ (0.6 g/L), $CaCl_2.2H_2O$ (0.8 g/L), $FeSO_4.7H_2O$ (0.1 g/L), $ZnSO_4.7H_2O$ (28 mg/L), $MnSO_4.H_2O$ (31 mg/L), $CoCl_2.6H_2O$ (73 mg/L), 500 $\mu$g/L of each of the following: thiamine, pantothenate, niacin, pyridoxamine, riboflavin, and thioctic acid, and 500 $\mu$g/L of each of the following: folic acid, biotin, and vitamin $B_{12}$. The basal medium was added to the first vessel in an amount of about 50% of the total culture media.

A 20% w/v glucose solution (Difco Laboratories of Detroit, Mich.) was autoclaved for a sufficient time and then cooled. The cooled glucose solution was added to the first vessel in an amount of about 5% of the total culture media to yield a glucose concentration of about 1%. De-ionized water was added to the first vessel in an amount of about 35% of the total culture media and then thoroughly mixed.

The inoculum obtained from the chopped PDA suspended in sterile de-ionized water was added to the culture media in an amount of about 10% of the total culture media to yield a culture broth. The formulation of the culture broth is shown below in Table 1.

TABLE 1

| COMPONENT | AMOUNT/LITER |
| --- | --- |
| 1) Basal medium | 500 ml |
| 2) 20% w/v Glucose Solution | 50 ml |
| 3) 1-mm plugs of *M. terrestris* suspended in sterile water | 100 ml |
| 4) Sterile water | 350 ml |
| 5) Nitrogen source | 1–6% w/v |

The culture broth was incubated at about 28° C. for about two to five days using a rotary shaker incubator (INNOVA 4000, New Brunswick Scientific in Edison, N.J.) agitated at about 300 rpm yielding the corresponding fungal mycelial biomass. This step may be repeated as necessary until desired fungal biomass size is achieved.

After about five days of incubation, the *M. terrestris* fungal biomass comprising mostly mycelia, was harvested and transferred to a larger culture vessel or shake flask in preparation for producing the microsclerotia. A microsclerotial culture media or final growth media, was prepared by adding to the larger culture vessel a microbial nutrient, or nitrogen source, selected from SOLULYS AST, in an amount of from about 3–6% of the total growth media, PHARMAMEDIA, in an amount of from about 3–4.5% w/v of the total growth media, or PROFLO in an amount of from about 3–4.5% w/v of the total growth media.

The basal medium as prepared above was added in an amount of about 50% of the total growth media to the larger vessel. A 20% glucose solution was autoclaved and then cooled. The 20% glucose solution was then added to the vessel in an amount of from about 20–30% of the total growth media to yield a glucose concentration of from about 4–6%, respectively. De-ionized water in an amount of from about 10–20% of the total growth media was added to the vessel, and the components were thoroughly mixed.

The fungal biomass prepared above was added to the growth media in an amount of 10% of the total growth media to yield a microsclerotial broth. A formulation of the microsclerotial broth is shown below in Table 2.

TABLE 2

| COMPONENT | AMOUNT/LITER |
|---|---|
| 1) Basal medium | 500 ml |
| 2) 20% w/v Glucose solution | 200–300 ml |
| 3) Mycelial biomass | 100 ml |
| 4) Sterile water | 100–200 ml |
| 5) Nitrogen source | 3–6% w/v |

The microsclerotial broth was incubated at a temperature of about 28° C. for about four to nine days using the rotary shaker incubator agitated at about 300 rpm to generate the corresponding microsclerotia. The resulting fugal biomass consisted primarily of fungal microsclerotia of *M. terrestris*.

During the initial growth period, the microsclerotial broth was extremely viscous and for the most part contained mycelia. Over time as the mycelia (i.e., hyphae) aggregated into microsclerotia, the microsclerotial broth became less viscous. By the fourth to the ninth day of incubation, mostly microsclerotia were observed in the microsclerotial broth. The number of the microsclerotia formed per liter of microsclerotial broth is shown below in Table 3 for the corresponding nitrogen source (i.e., microbial nutrient) and carbon source (i.e., glucose) concentrations.

TABLE 3

Mean Number of Microsclerotium Formed Per Milliliter of Culture Broth Containing Two Concentrations of Glucose and Two Concentrations of SOLULYS AST and PHARMAMEDIA

|  | 4% Glucose | | | | 6% Glucose | | | |
|---|---|---|---|---|---|---|---|---|
|  | SOLULYS | | PHARMAMEDIA | | SOLULYS | | PHARMAMEDIA | |
| % w/v | 3 | 6 | 3 | 4.5 | 3 | 6 | 3 | 4.5 |
| $10^3 \times$ Microsclerotia grown per mL of culture broth | 0.65 | 7.1 | 5.3 | 5.2 | 0.48 | 5.9 | 6.9 | 3.8 |

HYFLO diatomaceous earth from Celite Corporation in Lompoc, Calif., was added to the microsclerotial cultures in an amount of from about 5–10% w/v of the total microsclerotial broth. The microsclerotia-diatomaceous earth mixture was vacuum-filtered in a BUCHNER funnel using WHATMAN No. 1 filter paper. The filter cake was broken up, placed in shallow aluminum trays and air-dried overnight at a temperature of about 22° C. under a biological containment hood. When the moisture content was determined to be less than 5%, the dried microsclerotium-diatomaceous earth mixture was placed in polyethylene bags. The polyethylene bags were sealed under vacuum and stored at 4° C.

EXAMPLE 2

Evaluation of *M. terrestris* Microsclerotia Prepared in Example 1

Dried microsclerotia as prepared in Example 1 were evaluated to determine viability. The dried microsclerotia were spread on water agar plates and incubated at a temperature of about 28° C. for about 24 hours. After 24 hours of incubation, the number of microsclerotia present on the plate and the number of those germinating, were recorded to yield a percent germination result. The results of the evaluation are shown below in Table 4.

TABLE 4

Percent Germination of Dried Microsclerotium Prepared in Example 1 for the Corresponding Concentrations of Glucose and of SOLULYS or PHARMAMEDIA

|  | 4% Glucose | | | | 6% Glucose | | | |
|---|---|---|---|---|---|---|---|---|
|  | SOLULYS | | PHARMAMEDIA | | SOLULYS | | PHARMAMEDIA | |
| % w/v | 3 | 6 | 3 | 4.5 | 3 | 6 | 3 | 4.5 |
| Percent Germination | 9.5–93 | 21–37 | 71–75 | 51–90 | 58–89 | 73–98 | 91–100 | 97–100 |

Based on the results in Table 4, culture media comprising 6% glucose and 3–4.5% PHARMAMEDIA provided the best germination percentages at 91–100% and 97–100%, respectively. Microsclerotia produced in SOLULYS and 6% glucose was observed to possess excellent desiccation tolerance with a 58–98% survival rate after drying.

EXAMPLE 3

Sporogenic Germination of *M. terrestris*

Dried microsclerotia prepared from Example 1 were plated on water agar and incubated at room temperature for a few days for observation. Applicants have discovered that after one to three days of incubation, developing sporodochia (i.e., spore producing structures) emerged from the surface of the microsclerotia and microsclerotia initials. The sporodochia were observed developing, however the presence of spores was not evident until the fourth day. This has never been observed before in the art. The sporodochia advantageously provides spores, which serve as secondary infective units capable of infecting hydrilla. Prior art attempts to induce *M. terrestris* cultures to germinate sporogenically directly from the microsclerotia have been unsuccessful and have never been observed. Applicants further note that prior attempts at inducing *M. terrestris* to sporulate in culture on artificial media had been unsuccessful as confirmed in literature. Previously, *M. terrestris* has been observed to sporulate only under narrow conditions and the sporodochia have been observed to develop only directly on the surface of the host plant material (e.g., plant stems and leaves).

To further evaluate this discovery, Applicants plated about 0.05 g of the microsclerotia from Example 1 on water agar plates, and incubated the plated microsclerotia at a temperature of about 24° C. under various lighting conditions including natural light periods, 24-hour dark periods, and 14/10 photoperiods for three, six, nine, twelve and fifteen days, respectively. The results of this evaluation are shown below in Table 5.

TABLE 5

Number of Spores ($\times 10^6$) Produced from *M. terrestris* Microsclerotia Incubated on Water Agar at Room Temperature under 24-Hour Light Period, 24-Hour Dark Period, and 14/10 Photoperiod

| INCUBATION CONDITION | DAY 3 | DAY 6 | DAY 9 | DAY 12 | DAY 15 |
|---|---|---|---|---|---|
| Natural Light Period | 0 | 0.8 | 0.74 | 1.1 | 0.56 |
| 24 Hour Dark Period | 0 | 1.2 | 1.1 | 1.4 | 1.5 |
| 14/10 Photoperiod | 0 | 5.6 | 4.0 | 4.6 | 4.0 |

The results indicate that the microsclerotia prepared by the present methods are capable of germinating sporogenically under each of the conditions tested. The microsclerotia can germinate both as hyphae providing primary inoculum capable of penetrating and inducing disease in the host plant, and as spores to provide a secondary inoculum for attacking the host plant.

The forgoing discussion discloses and describes merely exemplary embodiments of the present invention. One skilled in the art will readily recognize from such discussion, and from the accompanying claims and examples, that various changes, modifications, and variations can be made therein without departing from the spirit and scope of the invention as defined in the following claims.

We claim:

1. A mycoherbicidal composition suitable for controlling the growth and population of target aquatic weeds, the composition comprising an aquatic weed population control effective amount of a microsclerotium of a fungal pathogen.

2. The mycoherbicidal composition of claim 1 wherein the fungal pathogen is a fungus deposited in the ARS patent culture collection having the assigned number NRRL 30559.

3. The mycoherbicidal composition of claim 1 further comprising an adjuvant selected from agrochemicals, biopesticides, herbicides, and combinations thereof.

4. The mycoherbicidal composition of claim 1 wherein the composition is in the form of dust, granules or pellets.

5. The mycoherbicidal composition of claim 1 wherein the fungal pathogen is *Mycoleptodiscus terrestris*.

6. The mycoherbicidal composition of claim 1 further comprising a suitable carrier.

7. The mycoherbicidal composition of claim 6 wherein the carrier is selected from the group consisting of diatomaceous earth, vermiculite, silica and clay.

8. The mycoherbicidal composition of claim 6 wherein the carrier is selected from the group consisting of wetting agents, humectants, absorptive agents, dispersants, surfactants, emulsifiers, gas producing disintegrants, glidants, slip agents, and combinations thereof.

9. A method for controlling the growth and population of target aquatic weeds, comprising applying an aquatic weed population control effective amount of the mycoherbicidal composition of claim 1 to a location in which the fungal pathogen can contact and infect the target aquatic weeds.

10. The method of claim 9 wherein the aquatic weed population control effective amount is at least ten microsclerotia/$cm^2$ of the location.

11. The method of claim 9 wherein the aquatic weed population control effective amount is from about 10 to 10,000 microsclerotia/$cm^2$ of the location.

12. The method of claim 9 wherein the aquatic weed population control effective amount is from about 100 to 2,000 microsclerotia/$cm^2$ of the location.

13. The method of claim 9 wherein the target aquatic weeds are selected from *Hydrilla verticillata* (L.f.) Royle ("hydrilla"), *Myriophyllum spicatum L.* ("Eurasian watermilfoil"), *Egeria densa L.* ("Brazilian Elodea"), and combinations thereof.

14. The method of claim 9 wherein the aquatic weed population control effective amount is from about 10 g to 100 kg per acre of the location.

15. A method for controlling the growth and population of target aquatic weeds, comprising applying an aquatic weed population control effective amount of the mycoherbicidal composition of claim 5 to a location in which the fungal pathogen can contact and infect the target aquatic weeds.

16. The method of claim 15 wherein the aquatic weed population control effective amount is at least ten microsclerotia/$cm^2$ of the location.

17. The method of claim 15 wherein the aquatic weed population control effective amount is from about 10 to 10,000 microsclerotia/$cm^2$ of the location.

18. The method of claim 15 wherein the aquatic weed population control effective amount is from about 100 to 2,000 microsclerotia/$cm^2$ of the location.

19. The method of claim 15 wherein the target aquatic weeds are selected from *Hydrilla verticillata* (L.f.) Royle ("hydrilla"), *Myriophyllum spicatum L.* ("Eurasian watermilfoil"), *Egeria densa L.* ("Brazilian Elodea"), and combinations thereof.

20. The method of claim 15 wherein the aquatic weed population control effective amount is from about 10 g to 100 kg per acre of the location.

21. A method for preparing a microsclerotium of a fungal pathogen having target aquatic weed population control activity, comprising growing the fungal pathogen under suitable growth conditions sufficient to compel the fungal pathogen to form a microsclerotium.

22. The method of claim 21 wherein the suitable growth condition is a nutrient-rich growth media.

23. The method of claim 22 wherein the nutrient-rich growth media is an aqueous liquid.

24. The method of claim 22 wherein the nutrient-rich growth media comprises a microsclerotium forming effective concentration of a nutritive substance selected from nitrogen sources, carbon sources and combinations thereof.

25. The method of claim 24 wherein the nitrogen sources are selected from the group consisting of cottonseed meal, corn steep, corn flour, digestible proteins, amino acids and mixtures thereof.

26. The method of claim 24 wherein the carbon sources are selected from the group consisting of monosaccharides, complex carbohydrates, and mixtures thereof.

27. The method of claim 24 wherein the microsclerotium forming effective concentration of the carbon source is at least 4% of the total growth media.

28. The method of claim 21 wherein the fungal pathogen is *Mycoleptodiscus terrestris*.

* * * * *